USO05561344A

United States Patent [19]

Hsi

[11] Patent Number: 5,561,344
[45] Date of Patent: *Oct. 1, 1996

[54] PHOTO-IONIZATION DETECTOR FOR DETECTING VOLATILE ORGANIC GASES

[75] Inventor: Peter C. Hsi, Alameda County, Calif.

[73] Assignee: RAE Systems, Inc., Sunnyvale, Calif.

[*] Notice: The term of this patent shall not extend beyond the expiration date of Pat. No. 5,393,979.

[21] Appl. No.: 399,493

[22] Filed: Mar. 7, 1995

Related U.S. Application Data

[63] Continuation-in-part of Ser. No. 61,419, May 12, 1993, abandoned.

[51] Int. Cl.⁶ ............................................. G01N 27/66
[52] U.S. Cl. .................. 313/494; 313/234; 313/607; 250/382; 250/379; 250/423 P; 324/464
[58] Field of Search ........................... 313/484, 574, 313/494, 594, 607, 234; 250/382, 379, 423 P; 324/464, 465

[56] References Cited

U.S. PATENT DOCUMENTS

| 515,465 | 2/1894 | Cottrell | 313/607 |
|---|---|---|---|
| 2,003,371 | 6/1935 | Koch | 313/234 |
| 2,015,885 | 10/1935 | Dällenbach | 313/607 |
| 2,017,897 | 10/1935 | Emersleben | 313/607 |
| 2,925,564 | 2/1960 | Shahbender | 313/607 |
| 2,959,677 | 11/1960 | Robinson et al. | |
| 3,531,685 | 9/1970 | Holz | 313/607 |
| 3,902,064 | 8/1975 | Young . | |
| 3,904,907 | 9/1975 | Young . | |
| 4,492,898 | 1/1985 | Lapatovich et al. | 313/607 |
| 4,792,732 | 12/1988 | O'Loughlin | 313/607 |
| 5,013,966 | 5/1991 | Saikatsu et al. | 313/607 |
| 5,117,160 | 5/1992 | Konda et al. | 313/607 |
| 5,393,979 | 2/1995 | Hsi . | |

FOREIGN PATENT DOCUMENTS

| 507533 | 10/1992 | European Pat. Off. | 313/607 |
|---|---|---|---|
| 2568409 | 1/1986 | France | 313/594 |

Primary Examiner—Sandra L. O'Shea
Assistant Examiner—Matthew J. Esserman
Attorney, Agent, or Firm—Flehr, Hohbach, Test, Albritton & Herbert

[57] ABSTRACT

A photo-ionization detector utilizes an ultraviolet (UV) lamp and is designed for detecting and measuring the concentration of volatile gases flowing between closely spaced parallel electrodes. One of the electrodes is formed to allow photons to pass into the space between the electrodes to ionize the volatile gases between the electrodes. The detector also incorporates an improved ionization chamber.

4 Claims, 2 Drawing Sheets

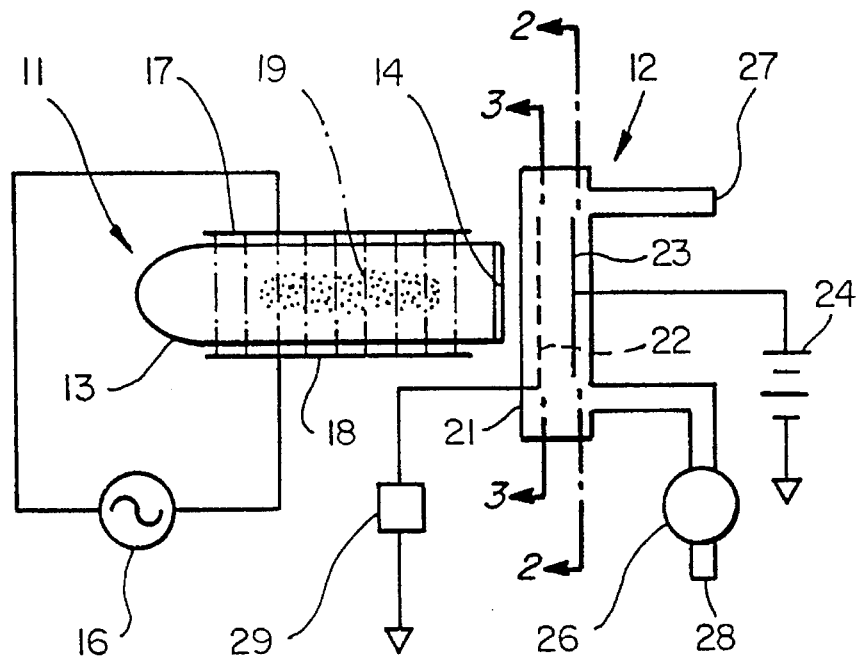
FIG_1
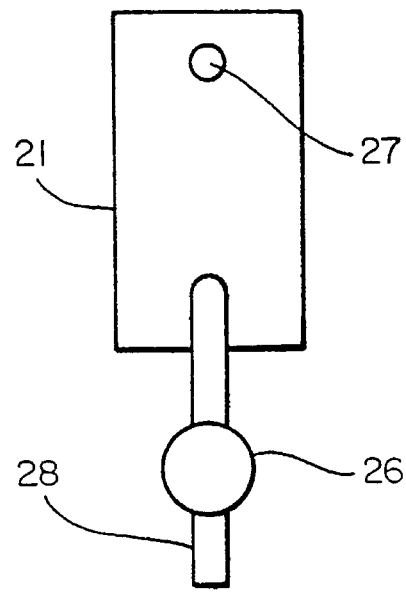
FIG_2

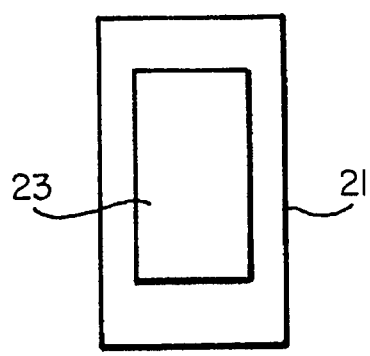
FIG_3
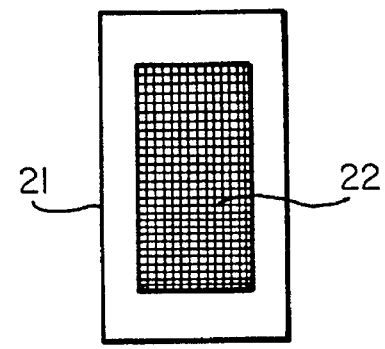
FIG_4
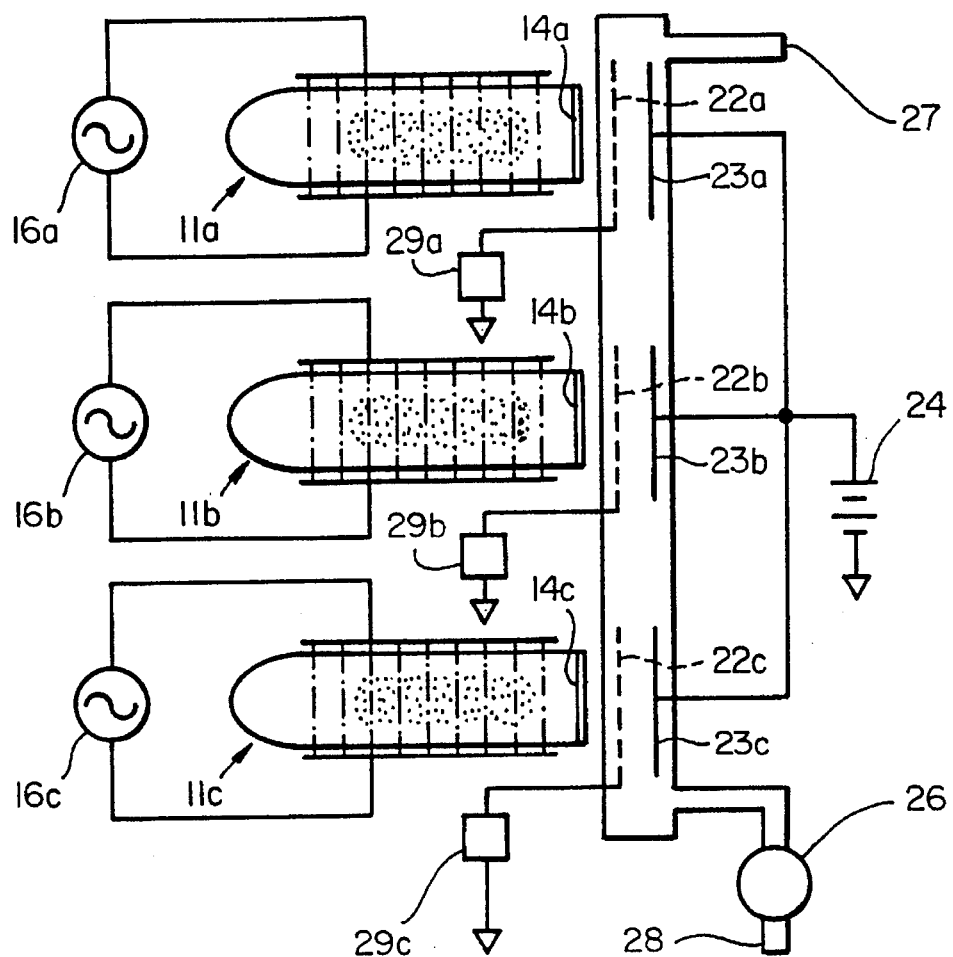
FIG_5

PHOTO-IONIZATION DETECTOR FOR DETECTING VOLATILE ORGANIC GASES

BRIEF DESCRIPTION OF THE INVENTION

This application is a Continuation-in-Part of application Ser. No. 08/061,419 filed May 12, 1993, now abandoned.

This invention relates generally to a photo-ionization detector for detecting and measuring the concentration of volatile organic gases, and more particularly to a photo-ionization detector having an improved ionization chamber and novel gas discharge UV lamp.

BACKGROUND OF THE INVENTION

Photo-ionization detection (PID) is a well-established method to detect volatile organic gas. The basic design of PID detectors includes a high-energy photon source, an ionization chamber, and a pair of electrodes. Typically, a gas discharge UV lamp is used as the high-energy photon source. This lamp produces photons with photon energy of 9.2 eV and above. When such high-energy photons hit organic gas molecules, molecules having ionization levels below the photon energy are ionized. In most PID instrument designs, the organic gas is brought into an ionization chamber by a pump. A UV lamp illuminates the chamber with high-energy photons. The resulting ions will cause a current flow between two electrodes disposed inside the chamber. An electrometer is used to measure the current. The current measurement can be converted into concentration in parts per million (ppm) of the organic gas based on the flow rate of the gas stream.

In a classical PID design, a glow discharge UV lamp is used to produce high-energy photons. The lamp is constructed with two electrodes placed inside a sealed glass envelope. The glass envelope is filled with certain gases, such as helium, argon or krypton. High voltage is applied between the two electrodes to induce an ionization process (i.e., separation of the electrons from the molecules). The ions and electrons are recombined shortly after to generate photons. These photons then pass through a UV window in the glass envelope to illuminate an associated ionization chamber.

A classical ionization chamber is constructed with an airtight housing and a pair of closely-spaced electrodes. The gas is introduced to the chamber through a small gas inlet and leaves the chamber through a gas outlet. The two electrodes are generally arranged in concentric form with one electrode in the middle of a cylindrical shaped electrode. A high-voltage DC (>150 V) is applied between the two electrodes to generate a high electric field. The UV window of the lamp is placed directly over the space between the two electrodes. When the gas molecules enter the chamber, they are ionized by the photons from the UV lamp. The resulting ions and electrons will be attracted to the two electrodes by the electric field. An electrometer measures the current flow.

The ionization chamber of the prior art has several disadvantages. The distance from the center electrode to the outside cylindrical electrode is relatively large (about the radius of the UV window). In order to achieve high electric field strength, relatively high voltage needs to be applied between the two electrodes. In addition, because of the long distance between the two electrodes, some ions and electrons will recombine before they reach the electrodes. As a result, the sensitivity of the detector is reduced. Once leaving the UV window of the lamp, the high energy photons travel a very short distance before they are absorbed by the organic gas molecules. Therefore, the region that photo-ionization process actually take place is just a few millimeters in front of the UV window. Beyond that region, the photo-ionization activity decreases rapidly. Therefore, in a classical cylindrical chamber design, the effective region for photo-ionization is limited only to the space right in front of the UV window. The gas molecules far from the UV window are unlikely to be ionized.

The prior art UV lamps, although useful in connection with the novel chamber of this invention, also have certain drawbacks, such as short life and low efficiency. In my co-pending application filed simultaneously herewith, there is described a novel gas discharge UV lamp particularly suitable for use in the photo-ionization detector of this invention.

The basic prior art photo-ionization detector has an inherent limitation: it cannot distinguish between different gases with similar ionization energy. When the high-energy photon hits a gas molecule, if the photon energy is higher than the ionization energy of the molecule, it will ionize it. By measuring the amount of ions and comparing it with a pre-defined reference value for that gas, the gas concentration can be calculated. However, there is usually more than one type of gas which has lower ionization energy than a specific photon energy. Therefore, for a given photon energy, these gas molecules can all be ionized. It is not possible to identify a specific gas and its correct concentration if the type of gas is unknown. In addition, if there is more than one type of gas present at the same time and the photon energy is higher than the ionization energy of these gases, it is also not possible to calculate the correct concentration of each individual gas.

This lack of specificity is a major drawback of present day PID instruments. They can be used to detect a single gas type. However, the user needs to know ahead of time what type of gas is being measured, and set the instrument calibration accordingly. Traditionally, a separation column is placed in front of the PID in order to separate the gas molecules before they enter the PID for detection and measurements.

The two most critical elements in the PID instrument design are the high-energy UV light source and the ionization chamber. A good UV light source produces stable UV light output and is very reliable and rugged. It also needs to be energy efficient, if it is to be used in portable battery-powered instruments. The chamber should be designed in such a way that even a very small number of gas molecules (less than one part per million) can be measured accurately. The instrument should be capable of distinguishing the type of gas.

OBJECTS AND SUMMARY OF THE INVENTION

It is a general object of this invention to provide a detector for detecting volatile gases.

It is another object of the invention to provide a volatile gas detector capable of detecting multiple volatile gases.

It is another object of the invention to provide a volatile gas detector which is efficient and simple in construction.

The foregoing and other objects of the invention are achieved by a detector that includes closely-spaced parallel electrodes for detecting the ionization of volatile gases flowing past electrodes by photons from a UV lamp.

BRIEF DESCRIPTION OF THE DRAWINGS

The foregoing and other objects will be more clearly understood by reading the accompanying description and the drawings, of which:

FIG. 1 shows a photo-ionization detector in accordance with one embodiment of the invention;

FIG. 2 is a rear elevational view of the photo-ionization detector of FIG. 1;

FIG. 3 is a sectional view taken along the line 2—2 of FIG. 1;

FIG. 4 is a sectional view taken along the line 3—3 of FIG. 1; and

FIG. 5 shows a photo-ionization detector in accordance with another embodiment of the invention;

DESCRIPTION OF PREFERRED EMBODIMENT(S)

The photo-ionization detector assembly, FIG. 1, includes a UV lamp 11 which radiates photons that enter an ionization chamber 12 to ionize volatile gas molecules in the chamber.

The UV lamp is of the type described in detail in my co-pending application filed herewith. For sake of completeness, the lamp will be briefly described. The lamp includes an envelope 13 which contains a mixture of gases such as helium, argon and hydrogen which can be ionized by an electric field to form electrons and ions which recombine to generate photons. For example, the gas mixture may be 30% helium, 30% argon and 40% hydrogen at a pressure of 10 Torr.

The gas molecules are ionized by an electric field 19 provided by applying a high AC voltage 16 to the spaced plates 17 and 18. For example, the voltage may be selected to provide a live electric field having an intensity of between 650 and 1250 volts at a frequency of between 40 and 100 kHz. A window 14 is formed at one end of the envelope and is selected to pass photons having predetermined energies.

The ionization chamber for the PID is a small cavity 21 of a few millimeters in thickness disposed in front of the UV window 14 of the lamp 11. Two parallel electrodes 22, 23 are placed very close to each other inside this cavity. In one embodiment the electrodes were spaced between 0.020 to 0.040 inches. A high DC voltage 24 is applied between these two electrodes. The gas is sucked into the chamber by a pump 26 through a small gas inlet 27. The gas is forced to pass through the cavity as a thin sheet of gas between the two electrodes. One electrode 22 is made of wire mesh so that the high-energy photons can shine through the mesh and excite the gas molecules when they pass in front of the UV window 14. The exhaust gas is let out of the chamber through a gas outlet 28. The ions collected on the electrode 22 is measured by an electrometer 29.

As described above, it is desirable in many instances to be able to detect and measure different types of volatile gases that may exist. In accordance with another embodiment of the invention, multiple gas discharge lamps 11a, 11b and 11c may be used in the same PID instrument. Multiple lamps 11a, 11b, 11c, FIG. 5, with different photon energies are used. The photon energy of each lamp is determined by the type of gases inside the lamp and the UV window 14 in the lamp which permits different wavelengths of UV light to pass. For example, in FIG. 5, the first lamp, 11a, has photon energy of 9.8 eV. The second lamp, 11b, has photon energy of 10.2 eV, and the third lamp, 11c, has 11.7 eV photon energy. These lamps are arranged in tandem to measure a given gas stream as it passes through the ionization chambers in front of each lamp. Individual mesh electrodes 22a, 22b, 22c are associated with electrodes 23a, 23b, 23c. In the example shown in FIG. 5, an electrometer 29a, 29b, 29c is associated with each pair of electrodes. As a result, the ion current associated with each lamp is measured and can be used to detect and determine the concentration of a corresponding gas. The UV discharge lamp can be turned on and off very rapidly. The new chamber design will also allow the PID to have instantaneous response to the photo-ionization process. Therefore, it is no longer necessary to keep the lamp on continuously. In this invention, the lamp is turned on long enough for the light output to be stabilized and the measurement taken. It is then turned off until next time for another measurement. The energy consumption of the lamp is greatly reduced. For example, in a typical application of PID instrument, the gas sample is usually measured at 1 second interval. Since it only takes about 100 ms to turn on the lamp and do the measurement, the actual "on" time for the lamp is only 1/10 of a second. Therefore, the total energy consumption for the new PID will be 10 times less than that of a conventional PID instrument.

The current can be measured during both the "on" period and "off" period of the lamp. Since there is no photo-ionization process during the "off" period, the measurement obtained during the "off" period is most likely due to other system noise or leakage current caused by moisture in the gas stream. By subtracting the "off" period measurement from the "on" period measurement, it is possible to eliminate some of the system errors and improve measurement accuracy.

This invention was incorporated in a miniaturized portable PID instrument. The lamp 11 was made of a glass tube, 0.5" in diameter and 1.8" in length. The glass tube was filled with helium and argon gases. Two copper plates of 0.5" by 1.5" were used as the electrodes 17, 18. An AC high-voltage source (1000 V peak to peak, 30 kHz) was connected to the electrodes. The resulting gas discharge glow and the UV light radiated through the UV windows at the end of the glass tube. The ionization chamber included two steel electrodes with a Teflon spacer (0.020" thick) between them. A DC voltage of 150 V was applied between the electrodes 22, 23. The instrument was sensitive to a gas level below 1 ppm.

What is claimed:

1. A photo-ionization detector for detecting and measuring a concentration of gases comprising:

an ionization chamber including a plurality of surfaces to form a volume of space wherein at least one of the surfaces is transparent to photons of predetermined energy;

means for introducing, moving, and removing gases in the ionization chamber;

planar spaced electrodes placed within the ionization chamber, wherein the electrode positioned closest to the transparent surface is formed to allow photons to pass through the electrode;

an ultraviolet (UV) light source including an envelope having a window which is transparent to photons having said predetermined energy, said window placed adjacent to said transparent surface, said envelope filled with a mixture of gases which can be ionized by an electric field to form electrons and ions which recombine to generate UV light having photons at said predetermined energy;

a pair of spaced plates disposed external to the envelope for providing therebetween the electric field which ionizes said mixture of gases to produce photons having said predetermined energy whereby the photons pass through said window, said transparent surface and said electrode to ionize gases within said ionization chamber;

means for establishing and maintaining an electric potential between the electrodes; and means for measuring the ion current flow generated from the ionized gases contacting said electrode.

2. A photo-ionization detector of claim 1 wherein the shape of the volume of space is relatively flat.

3. A photo-ionization detector as in claim 2 wherein the electrodes are spaced between 0.020 and 0.040 inches.

4. A photo-ionization detector of claim 1 wherein the electrode is made of wire mesh to allow the photons to pass through the electrode.

* * * * *

UNITED STATES PATENT AND TRADEMARK OFFICE
CERTIFICATE OF CORRECTION

PATENT NO. : 5,561,344
DATED : October 1, 1996
INVENTOR(S) : Peter C. Hsi

It is certified that error appears in the above-indentified patent and that said Letters Patent is hereby corrected as shown below:

Title page,
In the Related U.S. Application Data section, item [63]: , and in col. 1, line 6, Replace "Continuation-in-part of Ser. No. 61,419" with --Continuation-in-part of Ser. No. 61,418--.

Signed and Sealed this

Sixteenth Day of June, 1998

*Attest:*

BRUCE LEHMAN

*Attesting Officer*        Commissioner of Patents and Trademarks